United States Patent [19]

Pitts Crick et al.

[11] 4,421,392
[45] Dec. 20, 1983

[54] APPARATUS FOR DETECTING VISUAL FIELD DEFECTS OF THE EYE

[76] Inventors: Ronald Pitts Crick; Jonathan C. Pitts Crick, both of Pembroke House, Pembroke Rd., Sevenoaks, Kent, England

[21] Appl. No.: 74,809

[22] Filed: Sep. 11, 1979

[30] Foreign Application Priority Data

Sep. 12, 1978 [GB] United Kingdom ............... 36450/78

[51] Int. Cl.³ .............................................. A61B 3/02
[52] U.S. Cl. .................................. 351/224; 351/239; 351/243
[58] Field of Search ...................... 351/23, 24, 32, 35, 351/36, 37

[56] References Cited

U.S. PATENT DOCUMENTS 3,025,755  3/1962  Koetting ............................... 351/23

FOREIGN PATENT DOCUMENTS 12589  of 1899  United Kingdom ................. 351/32
925066  5/1963  United Kingdom ................. 351/23

OTHER PUBLICATIONS

Elliot (Editor), Basic Psychology,—1963 pp. 477 & 478.
Crick et al., The Application of Signal Processing Theory to Perimetry, Glaucoma Concepts, Research & Clinical Forms, 1980.

*Primary Examiner*—John K. Corbin
*Assistant Examiner*—Rodney B. Bovernick
*Attorney, Agent, or Firm*—Wenderoth, Lind & Ponack

[57] ABSTRACT

A perimeter for testing visual field light-sensitivity presents a moving spot or a set of fixed spots visually to a patient. The spot or spots have ill-defined edges so that the effect of visual acuity is minimized. A hand-held device is proposed whereby mass monitoring, particularly for the effects of glaucoma, is possible.

17 Claims, 6 Drawing Figures

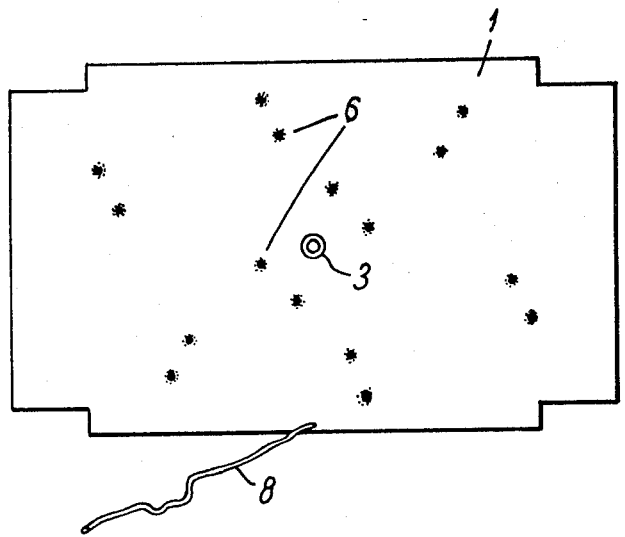
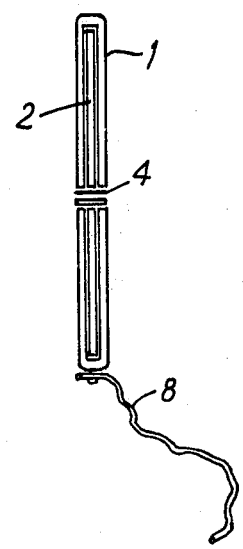
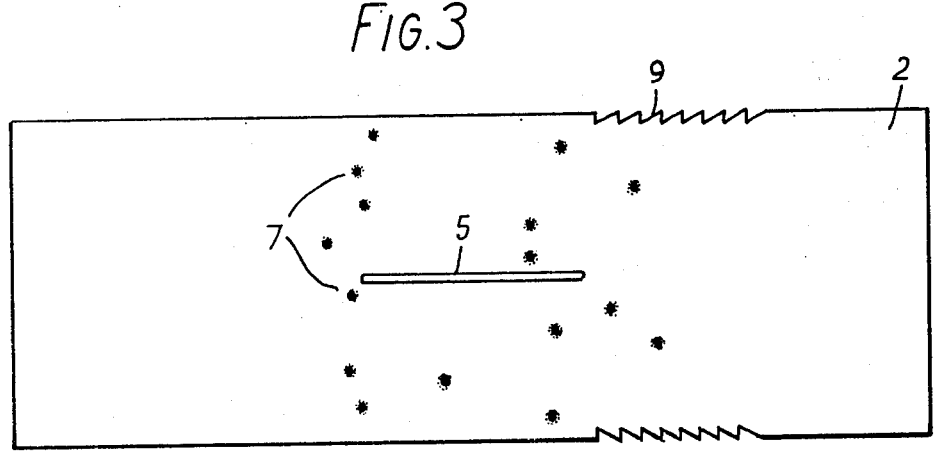

APPARATUS FOR DETECTING VISUAL FIELD DEFECTS OF THE EYE

BACKGROUND OF THE INVENTION

The invention relates to apparatus for detecting visual field defects of the eye. A particularly important application for such apparatus is in detecting and monitoring the effects of glaucoma.

Instruments are in use which display to a patient various patterns of light spots against a dark background and the practitioner is able to determine visual defects by analysis of those positions where spots are actually seen by the patient. Each pattern of spots is illuminated for a very brief period of time.

In another kind of instrument a single spot present continuously may be moved against a darker background. The positions in the predetermined locus of the spot which are observed by the patient are noted. These methods form the basis for all clinical visual field testing (perimeters). An example of such apparatus is that described in British Patent Specification No. 925,006. This instrument is generally known as the Friedman Analyser.

A difficulty not hitherto generally appreciated is that comparative analysis of visual field defects is difficult because the sensitivity of the eye to the stimulus depends upon whether it is in focus or not. Thus, spots which are not in focus are detected less readily than spots which are in focus. Strictly, perimeters are intended to examine the light-detecting ability of the eye rather than the acuity of the eye and it is therefore advisable to distinguish between the two abilities. This has not been done hitherto. One way of distinguishing light sense from defects in acuity due to refractive error is to insert a correcting lens suitable for each particular eye so that the spots are in focus in every case. However, this is generally not convenient.

SUMMARY OF THE INVENTION

The present invention makes it possible to reduce the effect of acuity in a light-detection test without the use of a correcting lens.

According to one aspect of the invention there is provided apparatus for detecting visual field defects of the eye comprising means for displaying to a patient a visual stimulus comprising one or more spots, the or each spot having a predetermined position or locus in the field of vision, and having ill-defined edges.

According to another aspect of the invention there is provided apparatus wherein the displaying means displays spots as a sequence of predetermined patterns, each pattern being displayed briefly.

Hitherto, the spots have had sharply defined edges. The use of spots with ill-defined edges ensures that in terms of acuity all patients are presented with similar stimuli, regardless within wide limits, of the visual acuity of the eye. It is therefore primarily the light-sensitivity of the eye which is being tested.

In certain apparatus the spots are discs with sharp edges or projected patches of light with sharp edges. In others they are defined by apertures in a screen or shutter plate. It is difficult to arrange ill-defined edges on a small aperture and while it is possible to envisage a fine comb-like structure at the edges of the aperture it is generally preferable to print a required pattern of graded density on a transparent film placed over the aperture. The printing may be effected photographically. As used herein "density" means the darkness of a dark spot of the brightness or a light spot.

The graduation of density may be in discrete steps and this may be effected by superimposing laminations of film of medium density with progressively larger and larger holes. Preferably, however, the graduation in density is continuous.

It has been found by the use of gratings as a means of assessing contrast sensitivity that a fall in visual acuity is associated with the loss of sensitivity to high spatial frequencies. Thus, in attempting to minimize the influence of visual acuity in visual field testing it is necessary to use stimuli which lack high frequency components and contain only those frequencies necessary to give adequate separation of the closest stimuli. On this basis, it is preferred to use a sinusoidal graduation of density across the diameter of the spot. However, other curves of similar form may serve equally well.

The invention may be employed with perimeters of any type. However, a particular requirement in the treatment and detection of glaucoma is for a simple and inexpensive device which may be used in the field by medical workers and general practitioners. Preferred features of the present invention provide such a device. Thus, preferably the apparatus comprises a screen with windows and a sheet held closely behind the screen, the sheet bearing images. Spots are presented to the patient by sliding the sheet behind the screen so that the images can appear briefly in the windows, and at least the windows having ill-defined edges. Preferably the images have ill-defined edges also. Conveniently the screen is in the form of an open-ended envelope within which the sheet slides, the envelope having different patterns of windows in its two sides. In this way the device is reversible and the number of available patterns for examination is doubled. Preferably the pattern of windows in one side of the envelope is the mirror image of the pattern in the other side.

A convenient way of displaying a pattern briefly to the patient is to arrange for a series of notches to be cut along at least one edge of the sheet, the sheet being pushed manually behind the screen to the extent of one notch at a time, the disposition of the images on the sheet giving different patterns of spots for the different notches. In this way a reasonably consistent time of display can be achieved.

It is necessary for accurate analysis to ensure that the patient has his eye fixed on a particular point of reference for all the tests. In accordance with a preferred aspect of the present invention the screen has a central aperture and the sheet has an open or transparent slot whereby the eye of the patient may be viewed through the screen. In this way the practitioner can ensure that for each test the point of fixation of the eye does not wander.

Another simple expedient provides that the screen is held at a pre-set distance from the eye. This is ensured by providing a distance cord of predetermined length fixed to the screen to be held against the cheek of the patient during examination.

BRIEF DESCRIPTION OF THE DRAWINGS

The invention will further be described with reference to the accompanying drawings, of which:

FIG. 1 is a front elevation of the envelope of a device embodying the invention;

FIG. 2 is a side elevation of the device;

FIG. 3 is an elevation of the slide sheet of the device;

DETAILED DESCRIPTION OF THE INVENTION

Figure 4:
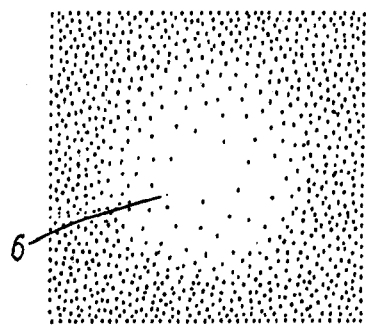
FIG. 4 is a diagram illustrating the nature of one of the windows of the envelope of the device.

Referring to FIGS. 1 to 3 the device comprises an open-ended envelope 1 within which slides a sheet 2. The envelope and sheet are made of suitable material such as card or plastic. The envelope has a central aperture 3 through which is fixed a rivet 4 and the sheet has a central slot 5 in which the rivet is registered to hold the sheet in the envelope. Thus, the sheet can slide within the envelope.

In each of its two sides the envelope has sixteen windows 6. For convenience these are not shown in FIG. 2. The sheet 2 has sixteen printed images shown at 7 in FIG. 3. The windows 6 are constituted by apertures covered with photographic film which is printed with a graduated pattern of optical density to be described further with reference to FIGS. 4 to 6.

In use, the envelope is held away from the face of a patient at a distance which is determined by a distance cord 8 fixed to the base of the envelope. Typically the cord is 30 cm in length. The end of the cord is held against the cheek of the patient and when the cord is taut the device is at the required distance from the eye. The patient gazes at the aperture 3 in the envelope. The practitioner looks through the aperture 3 and ensures that the eye of the patient is fixed on the aperture. Then the practitioner places his finger in the first of a series 9 of notches in the top edge of the sheet 2. The sheet is thereby pushed along to the extent of one notch. This has the effect of bringing into registration, in this example, two of the images 7 with respective windows 6. Each image passes completely across the respective window and appears only briefly. The practitioner asks the patient which images were seen and makes a note. The process is repeated for each of the notches. The different notches bring into registration different images with different windows so as to give different patterns of spots which are presented briefly to the patient's eye. A total of eight patterns is displayed. Then, the device is reversed and the pattern of windows and images on the reverse is the mirror image of the pattern on the front side. The process is repeated so that another eight patterns are displayed in turn to the patient. In this way a record can be made of the light sensitivity of different parts of the eye to the stimuli presented by the briefly appearing spots which are situated in the parts of the visual field shown experimentally to be most frequently impaired in glaucoma. Each pattern typically comprises two spots but in other examples patterns of three or more spots, or single spots, may be displayed. It will be noted that no two images are on the same horizontal line.

In this example the background presented by the basic shade of the envelope and sheet is grey. Although shown in FIGS. 1 and 3 for the sake of illustration as dark spots, the windows and images 6 and 7 give spots of lighter hue than the grey background. Grey is chosen in this embodiment instead of black in order to provide less variation of contrast between stimulus and background in lighting conditions which may be difficult to standardise accurately.

Referring now to FIG. 4 there is shown enlarged the nature of the density distribution of one of the windows 6 of envelope 1. This or a similar pattern is printed on photographic film across the window. The density of colouration (grey) diminishes from the outside to the centre of the window. The graduation of density is continuous and can be defined by a particular curve of density against distance.

Figure 5:
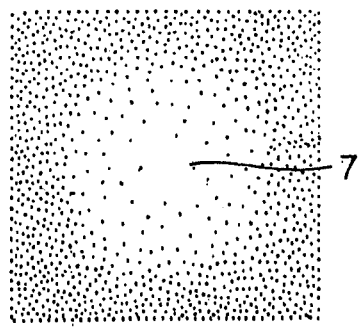
FIG. 5 is a diagram illustrating the nature of one of the images on the sheet of the device.
Figure 6:
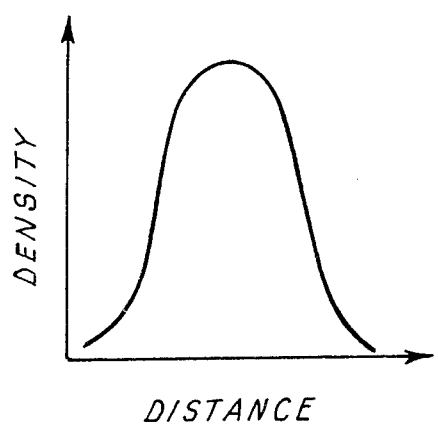
FIG. 6 a graph illustrating is the intensity characteristic of the spot presented by the superimposition of the image of FIG. 5 behind the window of FIG. 4.

The appearance of each spot to the eye depends not only upon the nature of the density distribution at the window 6 but also on the nature of the image 7 which passes behind the window. The nature of this image is shown in FIG. 5 and it will be seen it is of a similar nature to the density distribution of FIG. 4. It is to be understood that the square boundaries of FIGS. 4 and 5 are there to limit the size of the figures and in practice there is no such square boundary, the patches of brighter intensity merging continuously into the grey background. It will be seen that in view of the graduated density pattern of the spots they have edges which are ill-defined.

The curves of density distribution of the combination of the window 6 and the image 7 are such that when the window and the image are in registration the total density distribution is sinusoidal. This is represented by the curve in FIG. 6 which illustrates light intensity in the ordinate against distance across the spot in the abscissa. It is to be understood that the density distribution is symmetrical and is the same in all diameters of the essentially circular spot which appears to the observer.

The invention is not limited to the details of the foregoing embodiment described with reference to the accompanying drawings. For example, the spots may be dark against a light background.

Furthermore, the required nature of the spots in being ill-defined may be achieved by the use of a diffusing or refracting screen. The screen would be placed between the eye and perhaps conventionally sharp spots. A refracting screen may be constituted by a transparent sheet with a rippled surface, placed in use near the eye.

We claim:

1. An apparatus for detecting visual field defects of an eye of a patient, said apparatus comprising:
   means for displaying to a patient a visual stimulus comprising a plurality of spots having predetermined positions in the field of vision of the patient, each said spot having ill-defined edges to an extent such that said spot is incapable of being viewed by the patient as a sharply defined and outlined pattern regardless of the patient's visual acuity, said spots being characterized by stimuli which lack high frequency components and which contain only those frequencies necessary to give adequate separation of the closest stimuli.

2. An apparatus as claimed in claim 1, wherein said plurality of said spots comprise a sequence of predetermined patterns, each said pattern being displayed briefly.

3. An apparatus as claimed in claim 1, wherein each said spot is graduated in density from the center outwards.

4. An apparatus as claimed in claim 3, wherein the graduation in density is continuous.

5. An apparatus as claimed in claim 4, wherein said graduation in density has a sine-wave characteristic.

6. An apparatus as claimed in claim 2, wherein said displaying means comprises a screen having windows and a sheet bearing images, said sheet being positioned closely behind said screen and capable of sliding movement relative thereto so that said images appear briefly in said windows, thereby presenting said spots to the patient, at least said windows having ill-defined edges.

7. An apparatus as claimed in claim 6, wherein said screen comprises an open-ended envelope having two opposite sides between which said sheet slides, said two sides having therein different patterns of said windows.

8. An apparatus as claimed in claim 7, wherein said pattern of windows in a first said side of said envelope is the mirror image of said pattern of windows in a second said side of said envelope.

9. An apparatus as claimed in claim 6, wherein said sheet has along at least one edge thereof a series of notches, said sheet being pushed manually behind said screen to the extent of one said notch at a time, the disposition of said images on said sheet giving different patterns of said spots for different said notches.

10. An apparatus as claimed in claim 6, wherein said screen has therein an aperture and said sheet has therein a slot aligned with said aperture, wherein the eye of the patient may be viewed through said aperture and said slot.

11. An apparatus as claimed in claim 6, further comprising distance cord means of predetermined length connected to said screen for enabling said screen to be held a predetermined distance from an eye of the patient.

12. A method for detecting visual field defects of an eye of a patient, said method comprising:
displaying to the patient a visual stimulus comprising a plurality of spots having predetermined positions in the field of vision of the patient, each said spot having ill-defined edges to an extent such that said spot is incapable of being viewed by the patient as a sharply defined and outlined pattern regardless of the patient's visual acuity, said spots being characterized by stimuli which lack high frequency components and which contain only those frequencies necessary to give adequate separation of the closest stimuli; and
noting the ability of the patient to observe said stimulus.

13. An apparatus for detecting visual field defects of an eye of a patient, said apparatus comprising:
means for displaying to a patient a visual stimulus comprising a single spot having a predetermined locus in the field of vision of the patient, said spot having ill-defined edges to an extent such that said spot is incapable of being viewed by the patient as a sharply focused or defined and outlined pattern regardless of the patient's visual acuity, said spot being characterized by stimuli which lack high frequency components and which contains only those frequencies necessary to give adequate seperation of the closest stimuli.

14. An apparatus as claimed in claim 13, wherein said spot is graduated in density from the center outwards.

15. An apparatus as claimed in claim 14, wherein the graduation in density is continuous.

16. An apparatus as claimed in claim 15, wherein said graduation in density has a sine-wave characteristic.

17. A method for detecting visual field defects of an eye of a patient, said method comprising:
displaying to a patient a visual stimulus comprising a single spot having a predetermined locus in the field of vision of the patient, said spot having ill-defined edges to an extent such that said spot is incapable of being viewed by the patient as a sharply focused or defined and outlined pattern regardless of the patient's visual acuity, said spot being characterized by stimuli which lack high frequency components and which contains only those frequencies necessary to give adequate seperation of the closest stimuli; and
noting the ability of the patient to observe said stimulus.

* * * * *